United States Patent
Gryskiewicz et al.

(10) Patent No.: US 6,419,865 B1
(45) Date of Patent: *Jul. 16, 2002

(54) BONDED FLUFF STRUCTURES AND PROCESS FOR PRODUCING SAME

(75) Inventors: Stanley Michael Gryskiewicz, Woodstock; David Martin Jackson, Roswell; Jason Douglas Hadley, Atlanta; Jerome Joseph Schwalen, Marietta; Frank Paul Abuto, Duluth; Kuo-Shu Edward Chang, Roswell; Susan Carol Paul, Alpharetta; Richard John Schmidt, Roswell, all of GA (US)

(73) Assignee: Kimberly-Clark Worldwide, Inc., Neenah, WI (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/940,360

(22) Filed: Sep. 30, 1997

(51) Int. Cl.⁷ .................................................. D04H 1/60
(52) U.S. Cl. ........................ 264/122; 264/6; 264/113; 264/115; 604/378; 442/350; 442/351; 442/401; 442/59
(58) Field of Search .......................... 442/59, 350, 351, 442/401; 428/13; 264/6, 113, 122, 115; 604/378; 156/73.2

(56) References Cited

U.S. PATENT DOCUMENTS

| | | | |
|---|---|---|---|
| 3,950,218 A | * 4/1976 | Levesque | 162/201 |
| 4,219,024 A | * 8/1980 | Patience et al. | 128/287 |
| 4,426,417 A | 1/1984 | Meitner et al. | 428/195 |
| 4,761,258 A | 8/1988 | Enloe | 264/518 |
| 5,080,951 A | 1/1992 | Guthrie | 428/85 |
| 5,139,861 A | * 8/1992 | Williams et al. | 428/288 |
| 5,165,979 A | 11/1992 | Watkins et al. | 428/113 |
| 5,180,620 A | 1/1993 | Mende | 428/138 |
| 5,242,632 A | * 9/1993 | Mende | 264/6 |
| 5,540,872 A | 7/1996 | Ulman | 264/119 |

FOREIGN PATENT DOCUMENTS

| | | |
|---|---|---|
| EP | 317 058 | 5/1989 |
| EP | 533 982 | 3/1993 |
| GB | 2263914 | 8/1993 |
| GB | 2279673 | 1/1995 |
| JP | 02 074254 | 3/1990 |
| WO | 94 04736 | 3/1994 |

* cited by examiner

*Primary Examiner*—Terrel Morris
*Assistant Examiner*—John J. Guarriello
(74) *Attorney, Agent, or Firm*—Pauley Peterson Kinne & Erickson

(57) ABSTRACT

Bonded fluff structures and a method for producing such bonded fluff structures in which a pulp sheet having a material suitable for producing fluff and a heat activatable fiber material is fiberized to produce a mixture of fluff and heat activatable fibers. The mixture is contacted with a hot air stream, heating the heat activatable fibers to an activation temperature. The resulting heated mixture is then deposited onto a forming structure, forming a bonded fluff/fiber composite matrix structure.

15 Claims, 2 Drawing Sheets

BONDED FLUFF STRUCTURES AND PROCESS FOR PRODUCING SAME

BACKGROUND OF THE INVENTION

1. Field of the Invention

This invention relates to bonded fluff structures suitable for use as an absorbent material in personal care absorbent articles including diapers, feminine pads, incontinence garments, and training pants which is required to handle relatively large amounts of discharged body fluids, especially repeated discharges of relatively large amounts of fluid in relatively short periods of time, and a method for producing the same. More particularly, this invention relates to a fiberization process for producing such bonded fluff structures. In addition, this invention relates to a method for producing three-dimensional and density gradient bonded fluff structures for use in personal care absorbent articles.

2. Description of Prior Art

Personal care absorbent products such as diapers, feminine pads, adult incontinence products, and training pants often include a layer of absorbent material and a backing layer or moisture barrier which is impervious to fluid. The absorbent material includes a surface for contacting the body of the user so that body fluids are absorbed into the product and are contained by a moisture barrier.

Such absorbent materials are frequently formed as nonwoven fibrous webs, for example, fluff/binder/superabsorbent composite matrix structures. In order to maintain proper integrity when adhered to distribution materials to allow undisrupted capillarity across the boundary between such absorbent material structures and the distribution materials, and through the absorbent structure, it is necessary to bond the absorbent structure.

Conventionally, the body contacting surface of the absorbent materials in personal care absorbent articles is substantially flat and uniform. There are, however, several advantages to using a textured body contacting surface, such as a greater absorbent surface area and improved anatomical fit. The method of this invention is suitable for forming contoured fibrous webs or pads which have an increased weight of material in selected regions. When forming pads of absorbent material, the regions having the greater weight of material generally have a corresponding greater degree of absorbency. Such contoured absorbent pads are particularly useful in articles that are subjected to a greater fluid loading in certain "target" areas than in other areas. For example, in a baby diaper comprised of an absorbent bat or pad located between a liquid pervious inner layer and a liquid impervious outer layer, the crotch and front areas of the diaper are more heavily wetted by the infant than the areas closer to the infant's waist or back. A similar situation may also arise in the case of wound dressings, incontinence garments, and feminine sanitary napkins.

Developments in nonwoven technology have made tremendous strides over the past several years. Today, there exists a wide variety of technologies for forming nonwoven materials including meltblowing, spunbonding, melt spinning, solution spinning, carding, melt spraying, and wet/dry air laying. Many of these technologies are used individually to form single component materials. As an example, spunbonding is used to form nonwoven materials which can be used in such articles as workwear and personal care products including diapers. Meltblowing can be used to generate fine pore structures adaptable for use as filter media or absorbents for oil and other liquids. Air laying can be used to form such products as fibrous wood pulp bats for use as absorbents in diapers and sanitary napkins. In contrast to such processes which produce single component materials, the method of this invention is suitable for producing multicomponent materials.

Diaper dermatitis is a skin condition resulting from the prolonged contact of wet occlusive diapers with the skin of the wearer. This prolonged contact can lead to excessive hydration of the outermost skin layer, thereby reducing the skin's ability to function as a barrier. As a result, there is an increase in the permeation of irritants, susceptibility of the skin to physical damage, and invasion of the skin by microorganisms. Maintaining a normal skin hydration level helps the skin maintain its optimum barrier properties. Thus, it is important that personal care absorbent articles, to the extent possible, prevent excessive skin hydration while containing body exudates and providing a soft, dry and comfortable feel to the wearer.

Current occlusive absorbent garments with flap liners hold body exudates against the skin of the wearer. Heat and moisture are prevented from escaping from the product due to the close fitting nature of the product designed to prevent leakage. This problem is most severe in the insult region of personal care absorbent products. The flat liner provides a high contact area with the skin which can act as a pathway to conduct back to the skin free liquid that is not locked up by the absorbent core, especially when the product is under pressure at the insult point, because the flat liner cannot provide a sufficient degree of separation of the wearer from the free liquid. In addition, flat liners do not allow the insult region of the personal care absorbent product to communicate with the ambient air to allow humidity to be reduced in the insult region as well as away from the insult region.

There are a number of methods known to those skilled in the art for addressing these problems including the use of breathable back sheets, waist vents, and leg vents. However, these methods suffer from a variety of deficiencies which render them less effective than desired. For example, waist and leg vents through the back sheet tend to either be occluded against the skin or provide leakage pathways. Other known methods include the use of folded absorbent cores or layers under the liner to dry the liner. However, these methods require undesirable process options and economics. Three-dimensional absorbent fabrics, such as those produced in accordance with the method of this invention, can be used to address these issues.

SUMMARY OF THE INVENTION

Accordingly, it is one object of this invention to provide a method for bonding of fiber structures which maintain proper integrity when adhered to distribution materials so as to allow undisrupted capillarity across the distribution/fibrous structure boundary.

It is another object of this invention to provide a method of in-situ matrix bonding of fibrous structures using conventional product conversion machines without the addition of lengthy through air bonding ovens.

It is another object of this invention to provide an absorbent material for use in personal care absorbent articles, such as diapers and sanitary pads, having a density gradient.

It is yet another object of this invention to provide a bonded three-dimensional fluff structure for use in personal care absorbent articles.

These and other objects of this invention are achieved by a method for producing bonded fluff structures by which a pulp sheet comprising a material suitable for producing fluff and a heat activatable fiber material is fiberized, producing a mixture of fluff and heat activatable fibers. The mixture of fluff and heat activatable fibers is then contacted with a hot air stream at a flow rate and temperature sufficient to activate the heat activatable fibers without agglomeration of the mixture. The heated mixture is then deposited onto a forming structure, such as a forming wire, resulting in formation of a bonded fluff/fiber composite matrix structure.

In accordance with one embodiment of the method of this invention, the bonded fluff/fiber composite matrix structure is further processed in a manner which imparts a density gradient into the structure, for example, by passing the bonded fluff/fiber composite matrix structure through an embosser.

In accordance with another embodiment of the method of this invention, the bonded fluff/fiber composite matrix structure is shaped to form a bonded three-dimensional fluff structure.

BRIEF DESCRIPTION OF THE DRAWINGS

These and other objects and features of this invention will be better understood from the following detailed description taken in conjunction with the drawings wherein.

DEFINITIONS

Figure 1:
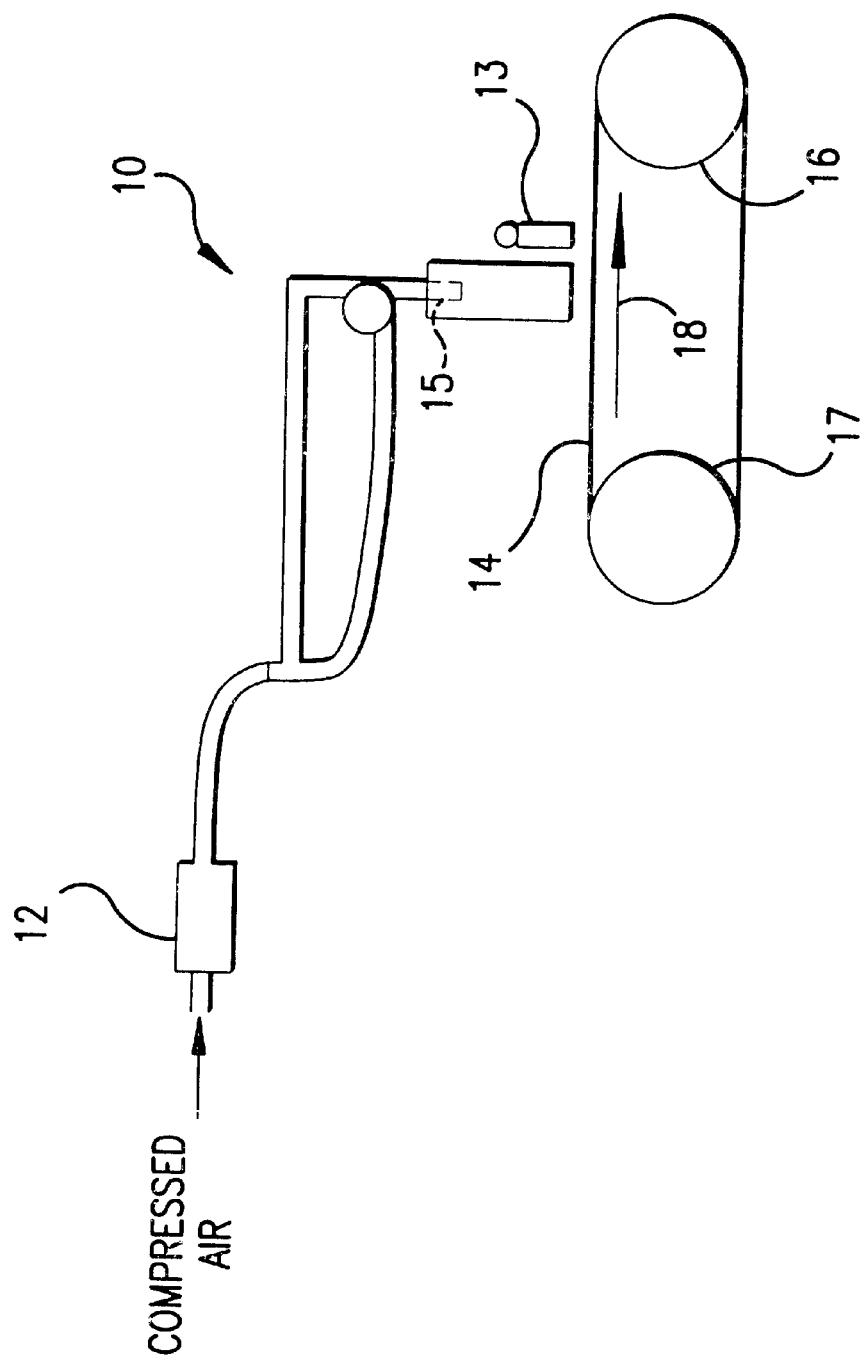
FIG. 1 is a schematic diagram of the hot air fiberization process used to produce the bonded fluff/fiber composite matrix structures in accordance with one embodiment of this invention.

As used herein, the term "nonwoven web" means a web that has a structure of individual fibers or threads which are interlaid, but not in an identifiable, repeating manner. Nonwoven webs have been, in the past, formed by a variety of processes such as, for example, melt-blowing processes, spunbonding processes, and bonded carded web processes.

As used herein, the term "polymer" generally includes, but is not limited to, homopolymers, copolymers, such as for example, block, graft, random and alternating copolymers, terpolymers, etc., and blends and modifications thereof. Furthermore, unless otherwise specifically limited, the term "polymer" includes all possible geometrical configurations of the material. These configurations include, but are not limited to, isotactic, syndiotactic, and random symmetries.

As used herein, the term "bicomponent fibers" refers to multicomponent fibers of various configurations including, but not limited to, side-by-side, core and sheath, pie segments, and islands in the sea configurations.

DESCRIPTION OF PREFERRED EMBODIMENTS

The method for producing bonded fluff structures in accordance with one embodiment of this invention comprises fiberizing a pulp sheet comprising a material suitable for producing fluff and a heat activatable fiber material resulting in formation of a mixture of fluff and heat activatable fibers. By the term "heat activatable" we mean a fiber which tackifies upon heating. Suitable materials for producing fluff include, but are not limited to, cellulosic materials. Any heat activatable polymeric fiber may be used to produce the bonded fluff/fiber composite matrix structure of this invention. A particularly preferred heat activatable fiber is a polypropylene/polyethylene polymer bicomponent binder fiber. Such bicomponent binder fibers tackify at a temperature of less than about 550° F. (288° C.), more particularly less than about 350° F. (177° C.).

After formation of the mixture of fluff and heat activatable fibers, the mixture is contacted with a hot air stream having a flow rate and a temperature sufficient to activate the heat activatable fibers. The heated mixture is then deposited onto a forming structure, such as a forming wire, resulting in formation of the bonded fluff/fiber composite matrix structure. The bonded fluff/fiber composite matrix structure is then densified, for example, in a nip. In accordance with one preferred embodiment of the method of this invention, prior to densifying, the bonded fluff/fiber composite matrix structure is further treated with a hot air knife to maintain the temperature of the structure at a desired level until it reaches the nip. A hot air knife, used for pre- or primary bonding a just produced microfiber to give it sufficient integrity, is a device which focuses a stream of heated air at a very high flow rate, generally from about 1000 to about 10000 feet per minute (fpm) (305 to 3050 meters per minute), or more particularly from about 3000 to 5000 feet per minute (915 to 1525 m/min.) directed at the nonwoven web immediately after its formation. The air temperature is usually in the range of the melting point of at least one of the polymers used in the web, generally between about 200 and 550° F. (93 and 290° C.) for the thermoplastic polymers commonly used in spunbonding. The control of air temperature, velocity, pressure, volume and other factors helps avoid damage to the web while increasing its integrity. The hot air knife's focused stream of air is arranged and directed by at least one slot of about ⅛ to 1 inches (3 to 25 mm) in width, particularly about ⅜ inch (9.4 mm), serving as the exit for the heated air towards the web, with the slot running in a substantially cross-machine direction over substantially the entire width of the web. In other embodiments, there may be a plurality of slots arranged next to each other or separated by a slight gap. The at least one slot is usually, though not essentially, continuous, and may be comprised of, for example, closely spaced holes. The hot air knife has a plenum to distribute and contain the heated air prior to its exiting the slot. The plenum pressure of the hot air knife is usually between about 1.0 and 12.0 inches of water (2 to 22 mmHg), and the hot air knife is positioned between about 0.25 and 10 inches and more preferably 0.75 to 3.0 inches (19 to 76 mm) above the forming wire.

The use of hot air during fiberization of fluff/bicomponent binder fiber pulp sheets activates the bicomponent fibers, thereby increasing the strength of the resulting composite matrix structure.

EXAMPLE

CR-54 pulp from U.S. Alliance Forest Products of Coosa Pines, Alabama and Danaklon ES-C polypropylene/polyethylene 2.0 dpf (denier per fiber), 6 mm bicomponent binder fibers from Danaklon a/s of Varde, Denmark were wet formed into pulp sheets. One of the sheets from this matrix of materials, 90% by weight CR-54/10% by weight Danaklon binder fiber, was fiberized on a six-inch continuous energy transfer (CET) fiberizer to produce a bonded fluff/fiber composite matrix structure. Although the process of this invention is described in terms of a CET fiberizer, there is no intention to limit the type of fiberizer used to produce the fluff/fiber mixture. Thus, for example, a hammermill fiberizer may be employed as opposed to a CET fiberizer. FIG. 1 is a schematic diagram of the hot air fiberization method of this invention utilizing a continuous energy transfer fiberizer. In this method, 500 cubic feet per minute of hot air was fed into a Chromalox 125 kilowatt air heater which was subsequently divided into two air sources that feed the fiberizer, tangential and stripper air. The temperatures and pressures at which this process was carried out are shown in Table 1:

TABLE 1

Temperature Ranges Used During the Trial

All Temperatures are in deg. F.

| | |
|---|---|
| Air Heater Temperature | 609–633 deg. F. |
| CET Outlet Temperature | 330–350 deg. F. |
| Down Stream Air Temperature | 500–522 deg. F. |
| Air pressure | 3.2 psig. |
| Forming Chamber Temperature | 388–393 deg. F. |
| Air Knife Temperatures | 310–355 deg. F. |

FIG. 1 is a schematic diagram of the continuous energy transfer fiberizer, in very general terms, used to form the bonded fluff/fiber composite matrix structure of this invention. CET fiberizer 10 comprises forming chamber 11 which contains the mixture of fluff and heat activatable fibers used in the formation of the composite matrix structure. Compressed air from a compressor (not shown) is heated in air heater 12 to a temperature in the range of about 350–700° F. (177–371° C.). The heated air is introduced through CET outlet 15 at a temperature of about 330–350° F. (165–177° C.) into forming chamber 11. The heated mixture of fluff and heat activatable fibers in forming chamber 11 is deposited onto collection or forming surface 14. As shown in FIG. 1, forming surface 14 is in the form of a continuous loop foraminous wire which travels in the direction of arrow 18. It will, however, be apparent to those skilled in the art that the collection/forming surface 14 may take other forms, such as the form of a rotating drum. Forming surface 14, as shown in FIG. 1, travels in the direction of arrow 18 about a pair of rollers 16, 17, either one or both of which may be driven. If desired, the speed of forming surface 14 can be variably driven so that the line speed can be controlled in relation to the deposition rates of the heated mixture of fluff and heat activatable fiber.

As previously stated, Table 1 shows the temperatures and pressures used during sample collection. The temperature of air heater 12 was about 609–633° F.; the temperature at the CET outlet 15 was about 330–350° F.; the temperature in forming chamber 11 was in the range of about 388–393° F. (198–201° C.); and the temperature of hot air knife 13 was in the range of 310–355° F. (154–179° C.). Samples were collected from the forming surface and pressure was placed on the materials by hand from a roller. Tensile strengths of the resulting material were measured, the results of which are shown in Table 2.

TABLE 2

| Control Tensile Strengths 200 g/m² web (Grams) | Heated-Air Sample Tensile Strength 200 g/m² web (Grams) |
|---|---|
| 59.2 | 157.92 |
| 59.2 | 177.66 |
| 78.96 | 157.92 |
| 98.7 | 177.66 |
| 74.01 ave. | 167.79 ave. |

As can be seen, tensile strengths for the bonded fluff/fiber composite matrix structure produced in accordance with the method of this invention using hot air fiberization were significantly higher than the control material, thereby clearly establishing that the heat activatable fibers were fused during fiberization. Indeed, tensile strengths for the hot-air formed samples were more than two times higher than tensile strengths of the samples formed without heated air. It is, thus, apparent that the method of this invention enables in-situ matrix bonding of fiber structures on conventional product converting machines without the addition of lengthy through air bonding ovens.

The bonded fluff/fiber composite matrix structure of this invention contains interfiber bonds throughout the structure. The temperature in the forming chamber 11 should be high enough to activate, that is tackify, the heat activatable fibers. The melted or heat activated fibers form substantially uniform interfiber bonds throughout the matrix structure, particularly at the fiber crossover contact points, providing a nonwoven web that is soft and strong. Illustrative articles that can be produced using the composite matrix structure of this invention include personal care absorbent products and components thereof, such as body-conforming sanitary napkin shells over an absorbent core, shape-retaining diaper components, incontinent care products, and the like.

Suitable polymers for use in the composite matrix structure of this invention are selected from the group consisting of polyolefins, polyamides, polyesters, polycarbonates, polystyrenes, thermoplastic elastomers, fluoropolymers, vinyl polymers, and blends and copolymers thereof. Suitable polyolefins include, but are not limited to, polyethylene, polypropylene, polybutylene, and the like.

Absorbent personal care articles such as sanitary napkins, disposable diapers, incontinent-care pads and the like are widely used, and much effort has been made to improve the effectiveness and functionalities of these articles. Thick, flat, personal care articles of the past that do not fit the shape of the human body and do not conform to the movements of the user have been largely replaced by resiliently conforming three-dimensional, body-shaped articles.

In accordance with one embodiment of the method of this invention, the bonded fluff/fiber composite matrix structure is shaped to form a bonded three-dimensional fluff structure. In particular, after the bonded fluff/fiber composite matrix structure exits forming chamber 11, it can be deposited onto a three-dimensional surface as is taught, for example, by U.S. Pat. No. 4,761,258. Through vacuum control and a male or female assist device, the bonded fluff/fiber composite matrix structure can be contoured to readily accept exudates. The resulting structure is resilient and holds its shape. In accordance with a further embodiment, a film layer can be applied during this process to allow formation of a product with a cavity. The structures produced in accordance with this embodiment are suitable for feminine care devices and BM inserts.

Figure 2:
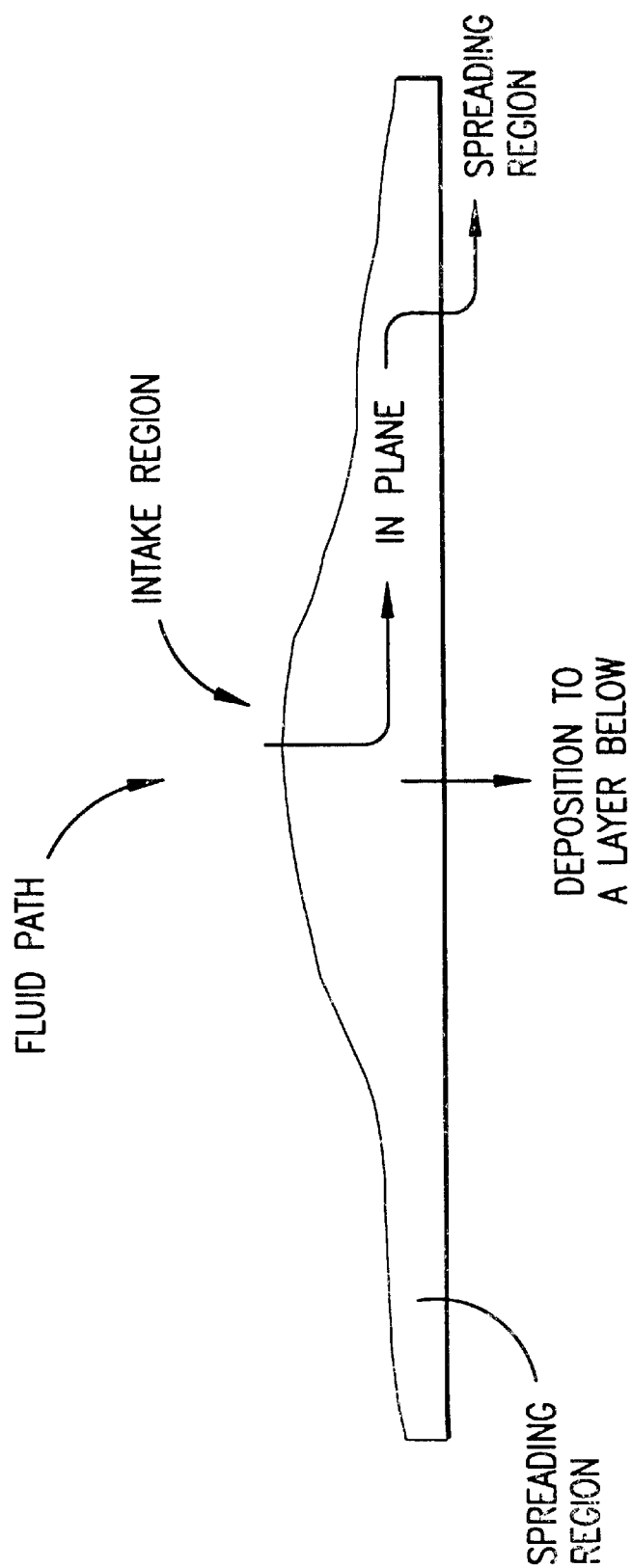
FIG. 2 is a schematic diagram showing a bonded fluff/fiber composite matrix structure comprising a density gradient in accordance with one embodiment of this invention.

In accordance with another embodiment of the method of this invention, the bonded fluff/fiber composite matrix structure is further processed in a manner which imparts a density gradient into the bonded fluff/fiber composite matrix structure. For example, after the fluff is deposited onto forming surface or forming wire 14, it can then be passed through an embosser which imparts a density gradient into the structure. In particular, an insert can be a fluff/superabsorbent material (SAM)/fiber composite and be configured less dense in the target zone and more dense as one moves away from this zone, thereby enabling fluid to be rapidly received and spread through the increasing dense regions. Because the structure is resilient, the intake area is ready for subsequent insult due to the fluid draining from this structure, through in-plane wicking and transfer and/or deposition into an underlying structure. Such a density gradient structure is shown is FIG. 2.

In accordance with one embodiment of the method of this invention, additional materials may be introduced into forming chamber 11 so as to provide the resulting composite matrix structure with additional desired features. For example, in accordance with one embodiment, a superabsorbent material is added to the fluff/fiber mixture in forming chamber 11. In accordance with another embodiment of this invention, an odor control material is added to the fluff/fiber mixture. It will be apparent to those skilled in the art that other additions which impart a variety of characteristics to the end product may also be incorporated into the fluff/fiber mixture.

While in the foregoing specification this invention has been described in relation to certain preferred embodiments thereof, and many details have been set forth for purpose of illustration, it will be apparent to those skilled in the art that the invention is susceptible to additional embodiments and that certain of the details described herein can be varied considerably without departing from the basic principles of the invention.

We claim:

1. A method for producing bonded fluff structures comprising the steps of:
   fiberizing a pulp sheet comprising one of a material suitable for producing fluff and a mixture of said material suitable for producing fluff and a heat activatable fiber material, and forming a mixture of fluff and heat activatable fibers;
   contacting said mixture with a hot air stream having a flow rate and a temperature sufficient to activate said heat activatable fibers, producing a heated said mixture; and
   depositing said heated mixture onto a forming structure, forming a bonded fluff/fiber composite matrix structure comprising bonded heat activated fibers.

2. A method in accordance with claim 1, wherein said bonded fluff/fiber composite matrix structure is densified in a nip.

3. A method in accordance with claim 2, wherein said bonded fluff/fiber composite matrix structure is treated with a hot air knife prior to said densifying.

4. A method in accordance with claim 1, wherein said heat activatable fibers are polypropylene/polyethylene polymer bicomponent binder fibers.

5. A method in accordance with claim 1, wherein said bonded fluff/fiber composite matrix structure is shaped to form a bonded three-dimensional fluff structure.

6. A method in accordance with claim 1, wherein said bonded fluff/fiber composite matrix structure is further processed in a manner which imparts a density gradient into said bonded fluff/fiber composite matrix structure.

7. A method in accordance with claim 6, wherein said density gradient is produced by passing said bonded fluff/fiber composite matrix structure through an embosser.

8. A method in accordance with claim 1, wherein said hot air stream is at a temperature less than about 550° F.

9. A method for producing bonded fluff structures comprising the steps of:
   introducing a fluff material and heat activatable fibers into a forming chamber, producing a fluff/fiber mixture;
   introducing a hot air stream into said forming chamber for a time period and at a temperature suitable for activating said heat activatable fibers, resulting in a heated mixture; and
   depositing said heated mixture onto a forming structure, forming a bonded fluff/fiber composite matrix structure comprising bonded heat activated fibers.

10. A method in accordance with claim 9, wherein said heat activatable fibers are polypropylene/polyethylene polymer bicomponent binder fibers.

11. A method in accordance with claim 9, wherein said bonded fluff/fiber composite matrix structure is shaped to form a bonded three-dimensional fluff structure.

12. A method in accordance with claim 9, wherein said bonded fluff/fiber composite matrix structure is further processed in a manner which imparts a density gradient into said bonded fluff/fiber composite matrix structure.

13. A method in accordance with claim 9, wherein said density gradient is produced by passing said bonded fluff/fiber composite matrix structure through an embosser.

14. A method in accordance with claim 9, wherein a superabsorbent material is added to said fluff/fiber mixture.

15. A method in accordance with claim 9, wherein an odor control material is added to said fluff/fiber mixture.

* * * * *

UNITED STATES PATENT AND TRADEMARK OFFICE
CERTIFICATE OF CORRECTION

PATENT NO. : 6,419,865 B1
DATED : July 16, 2002
INVENTOR(S) : Gryskiewicz et al.

It is certified that error appears in the above-identified patent and that said Letters Patent is hereby corrected as shown below:

Drawings,
Replace FIG. 1 with the following:

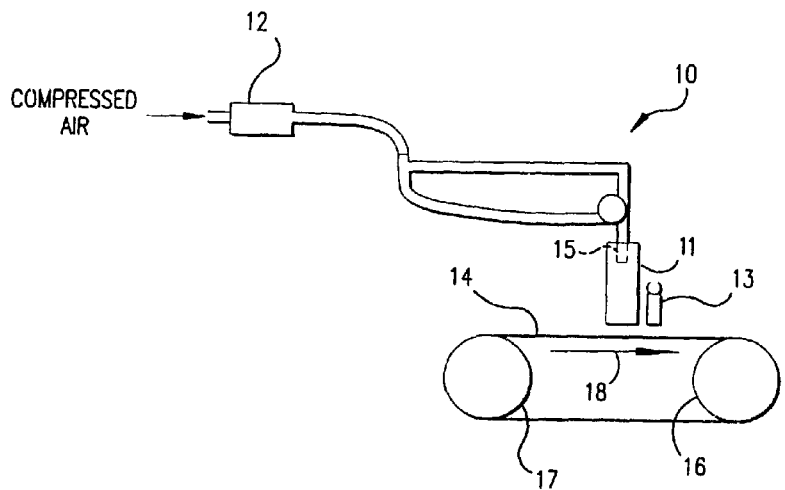

FIG. 1

Signed and Sealed this

Twenty-first Day of February, 2006

JON W. DUDAS
*Director of the United States Patent and Trademark Office*